United States Patent [19]

Parker et al.

[11] Patent Number: 4,541,438

[45] Date of Patent: Sep. 17, 1985

[54] LOCALIZATION OF CANCEROUS TISSUE BY MONITORING INFRARED FLUORESCENCE EMITTED BY INTRAVENOUSLY INJECTED PORPHYRIN TUMOR-SPECIFIC MARKERS EXCITED BY LONG WAVELENGTH LIGHT

[75] Inventors: John G. Parker, Olney; William D. Standbro, Columbia, both of Md.

[73] Assignee: The Johns Hopkins University, Baltimore, Md.

[21] Appl. No.: 500,345

[22] Filed: Jun. 2, 1983

[51] Int. Cl.[4] ............................................. A61B 6/00
[52] U.S. Cl. ....................................... 128/664; 424/9
[58] Field of Search ............... 128/664, 665, 633, 634, 128/395–398; 424/9; 250/361 C

[56] References Cited

U.S. PATENT DOCUMENTS

| | | | |
|---|---|---|---|
| 4,236,526 | 12/1980 | Richard | 128/633 |
| 4,266,549 | 5/1981 | Kimura | 128/665 X |
| 4,336,809 | 6/1982 | Clark | 128/665 |

OTHER PUBLICATIONS

Kinsey et al., "Endoscopic System ... Fluorescence", Rev. Sci. Inst. 51 (10), 1403–1406, Oct. 1980.
Dougherty et al., "Photoradiation Therapy ... Tumors", Cancer Research, vol. 38, pp. 2628–2635, Aug. 1978.
Doiron et al., "Fluorescence Bronchoscopy ... Cancer", Chest, 76:1, pp. 27–32, Jul. 1979.

*Primary Examiner*—Lee S. Cohen
*Attorney, Agent, or Firm*—Robert E. Archibald; Howard W. Califano

[57] ABSTRACT

An improved apparatus and method for optically localizing cancer lesions occluded beneath healthy tissue layers. A porphyrin tumor-specific marker is injected into a patient. After several days the healthy tissue has released the tumor-specific marker but the cancerous tissue has retained the tumor-specific marker. A long wavelength red excitation light illuminates an area of tissue and excites the porphyrin tumor-specific marker to fluorescence. An optical detection means monitors fluorescent emissions in the near infrared band and locates the source of the emissions.

31 Claims, 5 Drawing Figures

HPD FLUORESCENCE ABSORPTION AND EMISSION SPECTRA

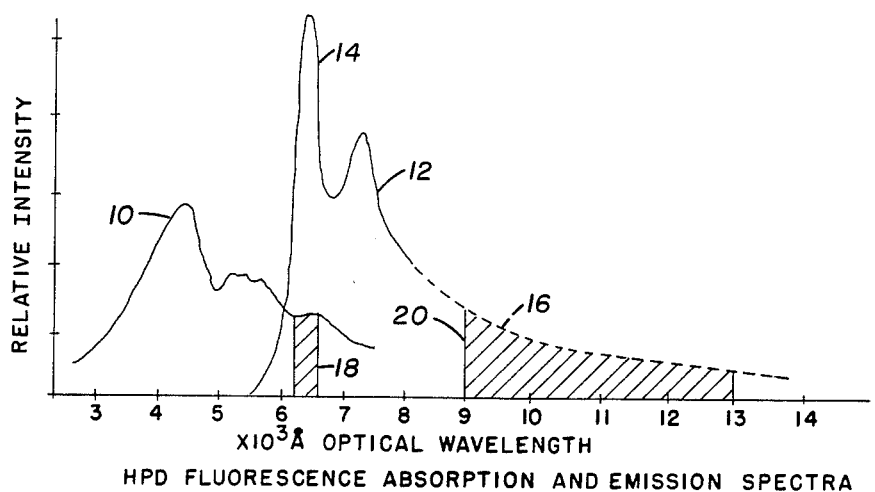
FIG. 1 — HPD FLUORESCENCE ABSORPTION AND EMISSION SPECTRA
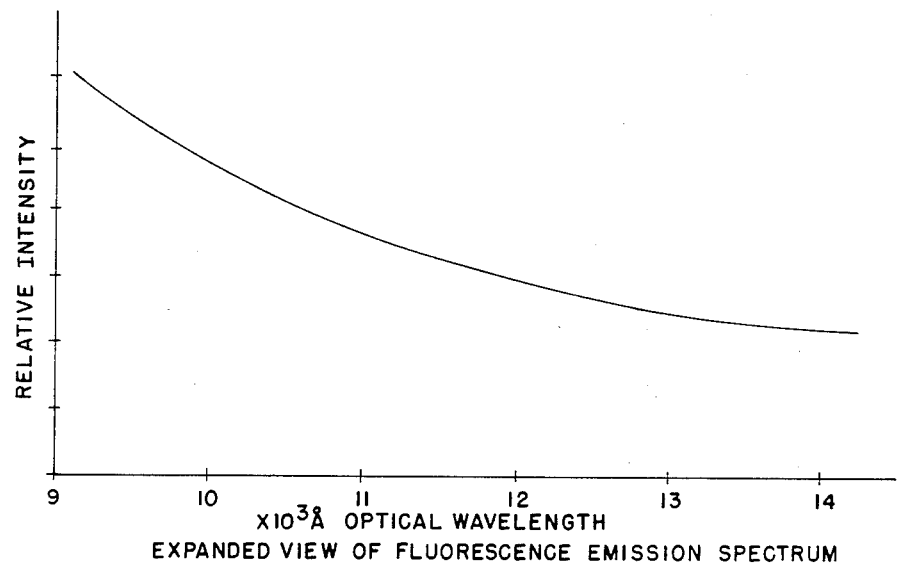
FIG. 2 — EXPANDED VIEW OF FLUORESCENCE EMISSION SPECTRUM
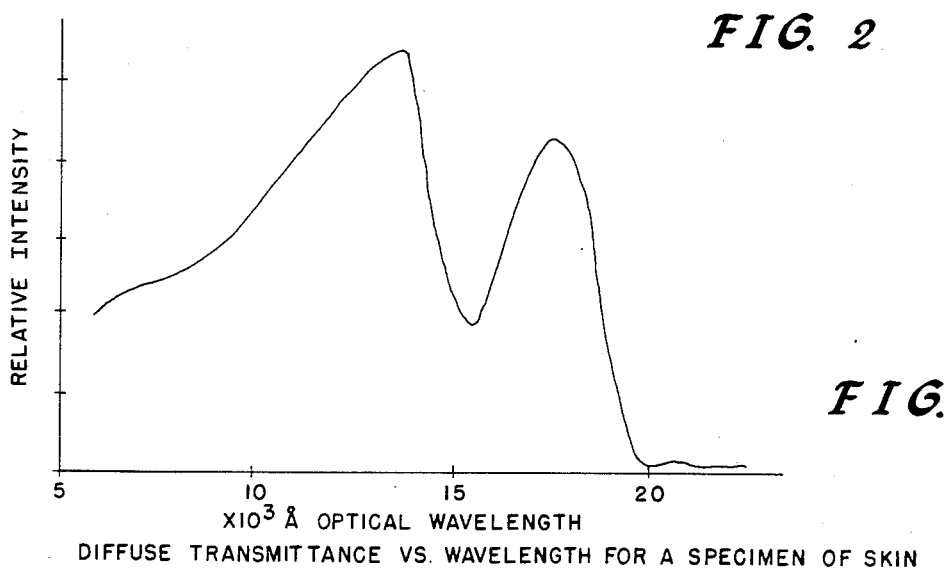
FIG. 3 — DIFFUSE TRANSMITTANCE VS. WAVELENGTH FOR A SPECIMEN OF SKIN

LOCALIZATION OF CANCEROUS TISSUE BY MONITORING INFRARED FLUORESCENCE EMITTED BY INTRAVENOUSLY INJECTED PORPHYRIN TUMOR-SPECIFIC MARKERS EXCITED BY LONG WAVELENGTH LIGHT

STATEMENT OF GOVERNMENTAL INTEREST

The Government has rights in this invention pursuant to Contract No. N00024-81-C-5301 awarded by the Department of the Navy.

BACKGROUND OF THE INVENTION

1. Field of the Invention

This invention comprises an improved apparatus and method for localizing cancer tumors on or near the tissue surface based on the use of long wavelength visible or near infrared excitation of intravenously injected porphyrins and monitoring the resultant infrared fluorescence.

2. Description of the Contemporary and/or Prior Art

There is a great deal of concern and interest in the medical and scientific community that an improved means to detect cancerous tumors be devised. In order to decrease the death rate due to cancer, early diagnosis, localization, and therapy must be undertaken. Early detection of tumor lesions of only a few millimeters in extent and 100 micrometers thick is possible by sputum cytology and immunodiagnostic procedures. However, such small preinvasive lesions are not localizable by conventional radiography, computer tomography or nuclear medicine techniques.

It is currently known that when certain porphyrin preparations, such as hematoporphyrin (HP) or hematoporphyrin derivative (HPD), are injected intravenously into the human body, they are selectively retained by cancerous tissue. Two or three days after injection, significantly higher levels of hematoporphyrin are retained in cancerous tissue. The selective retention of porphyrins, such as hematoporphyrin, by cancerous tissue has been used clinically as a "tumor-specific marker". It is known in the prior art that in the presence of ultraviolet or short wavelength visible light, the "tumor-specific marker" absorbed by the cancerous tissue will exhibit a bright red light fluorescence while normal tissue appears light pink.

A discussion of clinical investigations using the visible fluorescence of a "tumor-specific marker" to localize malignant tissue can be found in an article entitled "Hematoporphyrin Diacetate: A Probe to Distinguish Malignant from Normal Tissue by Selective Fluorescence" by R. W. Henderson, G. S. Christie, P. S. Clezy and J. Lineham, *British Journal of Experimental Pathology*, Volume 61, pp. 325-350 (1980). Another reference by D. R. Doiron and A. E. Profio entitled "Laser Fluorescence Bronchoscopy for Early Lung Cancer Localization" published in "*Lasers in Photomedicine and Photobiology*" (1980) teaches the use of a laser fluorescence bronchoscope to detect and localize small lung tumors by observing this red fluorescence.

Such prior art techniques have been used to develop endoscopes which use, in addition to the normal viewing white light, a supplementary violet light (at approximately 4200 Å). The violet light is used to excite hematoporphyrin or hematoporphyrin derivative, the tumor-specific markers which are dissolved in an appropriate buffer solution and intraveneously injected into the patient. The porphyrin tumor-specific marker is selectively retained by cancerous tissue and when exposed to the violet light emits a relatively bright red light fluorescence (at approximately 6,000-7000 Å), whereas the surrounding tissue emits only weakly. Similar techniques have been used to localize malignant tissue in the spleen, liver, bladder, kidney, and lungs.

The prior art techniques have one major limitation—only tumors on or near the tissue surface may be detected due to the high transmission loss of the short wavelength violet excitation light. This transmission loss is due to both absorption and scattering of the light by the patient's tissue and/or skin. Tumor lesions occluded by healthy tissue are not detectable using the prior art techniques.

SUMMARY OF THE INVENTION

Previous investigators did not realize that the fluorescence spectrum of porphyrins, such as hematoporphyrin or hematoporphyrin derivative, extends into the infrared band. An article by A. A. Krasnovsky, Jr. entitled "Photosynthesized Luminescence of Singlet Oxygen in Aqueous Solutions" printed in *BIOFIZIKA* 24: No. 4, pp. 747-748, 1979, describes long wavelength tails of emissions being present in aqueous solutions of riboflavin. However, Krasnovsky did not know whether the emissions were due to the fast fluorescence or (time delayed) phosphorescence of riboflavin.

The present inventors were the first to identify the origin of the long wavelength tail as a fluorescence emission and apply that observation in developing a method and apparatus of carcinoma localization. The present inventors while studying the generation of singlet oxygen by photoradiating hematoporphyrin and observing emissions in the 1.27 band, discovered infrared emissions consisting of: (1) a prompt fluorescence component of temporal duration equal to the laser exciting pulse of 10 nanoseconds: and, (2) followed by a temporally delayed, relatively slowly decaying, component due to radiative transition of singlet oxygen. Further research by the present inventors indicated that the prompt (or fast) fluorescence extended from the visible band (red light) into the infrared band (in excess of 14,000 Å). The infrared fluorescence component has the same origin, (i.e., fluorescence of the porphyrins) as did the red visible light known to other investigators. The overall fluorescence spectrum of porphyrins, such as hematoporphyrin or hematoporphyrin derivative, may thus be regarded as a superposition of a visible line spectrum and a continuous spectrum extending from 6,000 Å to substantially in excess of 14,000 Å.

The inventors recognized that detecting the presence of a porphyrin tumor-specific marker, such as hematoporphyrin or hematoporphyrin derivative, retained by the cancerous tissue could be enhanced, if the infrared portion of the fluorescence emission spectrum were used as opposed to the visible portion of the spectrum as used in the prior art. Use of the infrared emission spectrum allows the inventors to choose an excitation frequency band and a diagnostic frequency band which are physiologically selected to deliver maximum optical signal penetration into human or animal tissue. The prior art technique used a violet excitation light primarily because of its spectral separation from the known visible fluorescence band (6,200-7,500 Å). Spectral separation is necessary so that the fluorescence diagnostic signal, which is temporally co-existent with the excitation pulse, can be resolved and detected.

The invented technique thus allows the selection of excitation and diagnostic bands having minimal transmission losses through human and animal tissue. For example, red light (6,200–6,400 Å) could be used as the excitation source and would provide significantly reduced transmission losses compared to the prior art short wavelength or violet excitation frequencies. Similarly, use of a diagnostic band at the infrared wavelength of 9,000–13,000 Å could be chosen to provide sufficient spectral separation from the visible red excitation frequency and to provide maximum signal transmittance through animal or human skin and tissue.

The present invention thus discloses a method and apparatus for improving the sensitivity and maximizing the penetration depth of fluorescent cancer localization techniques. In the preferred embodiment, maximum tissue penetration is provided by detecting fluorescence emission in the infrared band in conjunction with a red light excitation source. This combination will optimize signal penetration below the surface thus permitting detection of occult tumors.

A first novel feature is the use of the fluorescence emission, generated by porphyrin tumor-specific markers in the infrared portion of the spectrum, as a means for localizing cancerous tissue having selectively absorbed the tumor-specific marker.

A second novel feature is the selection of an excitation frequency physiologically chosen to provide maximum signal transmittance, so that tumor lesions occulted by healthy tissue can be detected and localized.

A third novel feature is the selection of an excitation frequency which provides spectral separation between the execitation frequency and the diagnostic band so that the diagnostic infrared emission signal can be resolved and detected.

A fourth novel feature is the selection of a diagnostic band in the infrared frequency range, physiologically chosen to provide maximum signal transmittance, so that tumor lesions occulted by healthy tissue can be detected and localized.

A fifth novel feature is a method and apparatus of carcinoma localization based on the use of long wavelength visible (red) or near infrared excitation of intravenously injected porphyrins, such as hematoporphyrin or hematoporphyrin derivative, and monitoring the resultant infrared fluorescence.

These features, as well as other objects and advantages of the present invention, will become readily apparent after reading the ensuing description of several non-limiting illustrative embodiments and viewing the accompanying drawings.

BRIEF DESCRIPTION OF THE DRAWINGS

FIG. 1 is a graph illustrating the absorption and fluorescence emission spectrum for hematophorphyrin derivative (HPD), a typical porphyrin tumor-specific marker.

FIG. 2 is an expanded graph showing the infrared fluorescence spectrum of hematoporphyrin (HP), a typical porphyrin tumor-specific marker.

FIG. 3 is a graph showing the transmittance of a light beam through human skin as a function of wavelength.

DETAILED DESCRIPTION OF THE PREFERRED EMBODIMENT

Figure 4:
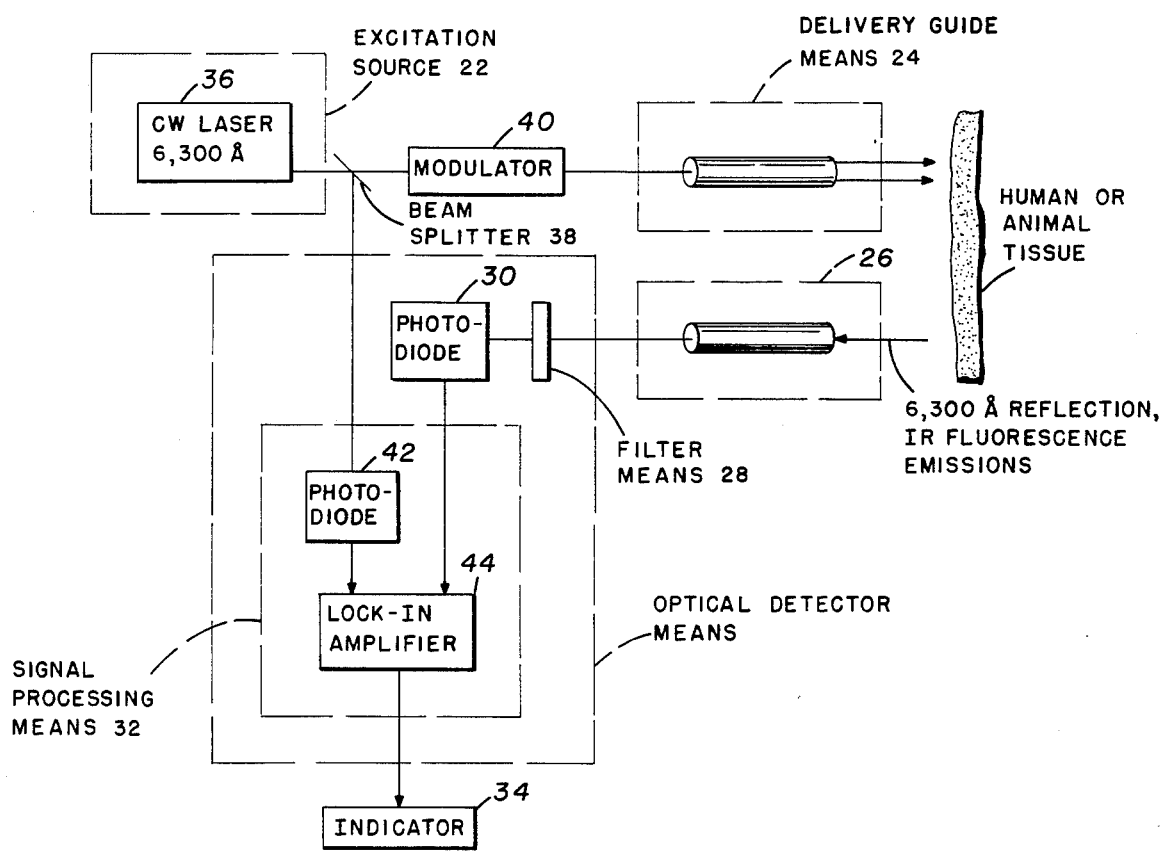
FIG. 4 is a block diagrammatic view of the present invention when a substantially continuous excitation beam is used.

The absorption and fluorescence emission spectra for hematoporphyrin derivative, a typical porphyrin tumor-specific marker, are illustrated in FIG. 1. The absorption spectrum 10 has a peak at approximately 4,000 Å, the violet range, and then falls off at the upper end to a frequency of approximately 7,000 Å. The fluorescence emission spectrum 12 contains a superposition of a visible line spectrum 14 and a continuous spectrum extending from 6,000 Å into the infrared band 16 (in excess of 14,000 Å). The infrared portion of the spectrum 16, as observed by the inventors, is shown by the dotted portion of the emission spectrum 12.

The prior art techniques irradiate the porphyrin tumor-specific markers at their maximum absorption wavelength of 4,000 Å (violet light) and observe the porphyrin's visible red fluorescence at 6,000–7,000 Å. The prior art techniques select the excitation and diagnostic frequency for maximum absorption of the excitation signal and maximum fluorescence emission by the porphyrin. However, the prior art techniques do not consider the frequency dependence of light transmission through human tissue and/or skin. The present invention photoradiates the porphyrin with visible red light 18 in the 6,200–6,400 Å band. As we shall see later in this application, this frequency is chosen to optomize signal transmittance through human or animal tissue. The present invention selects the infrared section of the spectrum between 9,000–13,000 Å as the diagnostic frequency band 20. This band is selected to optimize: (1) spectral separation from the excitation frequency to allow resolution and detection of the diagnostic infrared fluorescence; and, (2) transmittance of the diagnostic infrared fluorescence through the particular tissue and/or skin.

FIG. 2 illustrates an expanded view of the infrared emission spectrum for hematoporphyrin, a typical porphyrin tumor-specific marker. The fluorescent emission spectrum in the infrared band is a slowly decreasing function of increasing wavelength which appears to be approximately a straight line when plotted on semilogarithmic graph paper. The discovery of the infrared portion of the emission spectrum allows the inventors the flexibility to select the excitation and diagnostic bands so as to maximize signal transmittance through tissue.

FIG. 3 is a graph illustrating the transmittance of a light beam through human skin as a function of wavelength. The signal transmittance, which is reduced by absorption and reflectance of the tissue, directly increases with frequency from the visible light band into the infrared band and then rapidly falls off after 13,000 Å. If the invented apparatus were used to localize tumor lesions below the skin surface, the excitation and detection band should be chosen to maximize signal penetration through the skin. The excitation frequency would be chosen to optomize both optical transmittance (see FIG. 3) and signal absorption by the porphyrin (see FIG. 1). If hematoporphyrin is used as the tumor-specific marker and the tumor is located the beneath skin, the red visible frequency band (6,200–6,400 Å) is advisable. Similarly, the diagnostic frequency band is selected to: (1) assure sufficient spectral separation from the excitation frequency so that the fluorescence diagnostic signal can be resolved and detected; and, (2) choose a frequency band in the infrared range which has maximum signal transmittance through the skin or tissue and at the same time allows maximum collection of the fluorescent emission. In the above example, with a red visible excitable beam the inventors have found a fluorescence diagnostic band at 9,000–13,000 Å to be satisfactory.

It is to be understood, however, that different tissue or skin types will have a different frequency dependent optical transmittance curve, and that various porphyrin tumor-specific markers will have absorption and infrared flourescence spectrums which differ slightly from that shown in FIGS. 1. and 2. However, it is within the contemplation of this invention to use the above-described method to select an excitation frequency band and an infrared diagnostic frequency band so as to optimize the ability of the present invention to penetrate below the skin or tissue surface thus permitting the detection of occulted tumors.

Porphyrin other than the previously discussed hematoporphyrin (HP) and hematoporphyrin derivative (HPD), can act as tumor-specific markers. To qualify as a tumor-specific marker in accordance with the present invention, any photosensitive dye may be used which satisfies the following categorical requirements:

1. must be optically absorbing at wavelengths greater than 6,000 Å;
2. must be non-toxic;
3. must be injectable into the blood stream, i.e., water-soluble;
4. must be selectively retained by cancerous tissue;
5. must exhibit significant infrared fluorescence.

Porphyrins which pass the above criteria and which have been used in addition to hematorphyrin (HP) and hematorporphyrin derivative (HPD) include, tetra carboxyphenylporphine (TCPP), tetraphenylporphinesulfonate (TPPS), tetra (4-N-methylpyridil) porphin (TMPP), protoporphyrin, coproporphyrin and uroporphyrin. It appears that water soluble (and thus injectable) porphyrins as a group act as tumor-specific markers as taught by the present invention although experimentation to date indicates that hematoporphyrin (HD) and hematoporphyrin derivative (HPD) are the two most promising candidates.

It will be noted that hematoporphyrin derivative (HPD) according to R. Bonnett, R. J. Ridge, P. A. Scourides and M. C. Berenbaum, *J. Chem. Soc. Chem. Comm.*, pp. 1198–1199 (1980) is a multicomponent substance containing the following basic components: acetylhematoporphyrin, diacetylhematoporphyn and acetoxyethylvinyldeuteroporphyrin, protoporphyrin, and tumor-sensitive marker.

Other types of photosensitive dyes which are of interest include riboflavin, fluorescein, acridine orange, tetracyclines and berberine sulfate.

Figure 5:
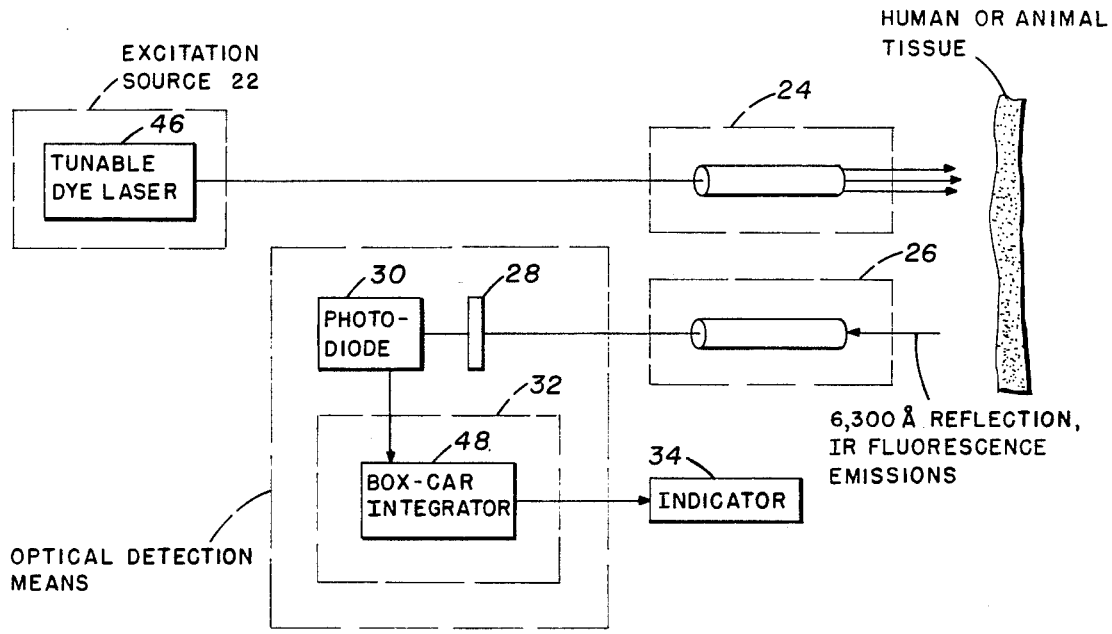
FIG. 5 is a block diagrammatic view of the present invention when a pulsed excitation beam is used.

FIGS. 4 and 5 illustrate, in block diagrammatic form, the invented apparatus used to localize carcinoma lesions. The apparatus generally contains: a source of excitation light 22 (generally in the red visible frequency band) which can be either continuous or pulse modulated; a delivery guide means 24 for directing the excitation beam to the appropriate point within the patient's body (the delivery guide means may include a fiber optical delivery system in association with an endoscope such as described in U.S. Pat. No. 4,072,147 or a diagnostic radiator such as described in U.S. Pat. No. 4,336,809 for injection in the tumor mass); a return guide means 26 for collecting both the reflected excitation signal and the infrared fluorescence emission from the porphyrin tumor-specific marker; a filter means 28 for allowing the passage of fluorescence emission in an appropriate portion of the infrared band; a photodiode 30 which detects the infrared fluorescence; signal processing means 32 operably connected to said photodiode 30 for providing an electrical output signal varying as a function of the intensity of infrared fluorescence; and, an audio and/or visual indicator 34 for alerting the physician of the location of carcinoma lesions.

In operation, the patient is injected with a tumor-specific marker, such as hematoporphyrin or hematoporphyrin derivative, which after two or three days lapse time is selectively retained by malignant tissue. The delivery guide means 24 and return guide means 26 are normally incorporated into a double fiber optical delivery system used in association with a diagnostic radiator or endoscope such as described in U.S. Pat. No. 4,072,147. The endoscope type device is brought in proximity to the tissue which is to be tested. The delivery guide means 24 causes a portion of the tissue area to be illuminated by the excitation beam. The return guide means 26 normally has a narrow beam width allowing the physician to determine if a particular spot emits the infrared fluorescence associated with the tumor-specific marker. The endoscope type device, normally contains a viewing telescope allowing the physician to note the particular spot to return guide means 26 is pointed towards. The audio or visual indicator 34 alerts the physician when an infrared fluorescent signal is detected. In this manner, the physician scans the tissue area and in response to the audio/visual indicator 34 locates malignant lesions.

FIG. 4 is a block diagrammatic view of the invented apparatus when a substantially continuous excitation source is used. The apparatus generally consists of: a CW laser 36, which in the preferred embodiment generates an excitation beam at 6,300 Å; a beam splitter 38 which produces two spacial components of the excitation beam; a modulator 40, such as an acousto-optic modulator for chopping the excitation beam; a delivery light guide mean 24 and a return guide means 26 which, as discussed previously, can be incorporated into a double fiberoptic delivery system used in association with a diagnostic radiator or an endoscope; a filter 28 which allows the passage of a selected portion of the infrared fluorescence spectrum; a photodiode 30 which may be an InGaAs diode, a germanium diode or a silicon diode; a second photodiode 42; a lock-in amplifier 44 which receive as inputs electrical signals from photodiode 30 and photodiode 42 and produces an output signal responsive to the amplitude of the detected infrared fluorescence; and, an indicator 34 which generate an audio and/or visible signal to alert the physician when a detected infrared fluorescence diagnostic signal is received by the return guide means 26. It is to be understood that the CW laser can be tunable to deliver an excitation beam having a frequency selectable for maximum tissue penetration and also maximum dye absorption as taught by the present invention. It is also to be understood that various audio/video indicators may be used to alert the physician and various delivery and return guide means can be used to deliver the excitation beam and collect the infrared fluorescence emissions.

FIG. 5 is a block diagrammatic view of the present invention when a pulsed or chopped excitation source is used. The apparatus generally consists of: a tunable dye laser 46, providing an excitation beam (in the preferred embodiment an excitation signal of 6,300 Å is used); a delivery guide means 24 and return guide means 29 for selectively radiating tissue with the excitation beam and collecting any infrared fluorescence emitted from said radiated tissue (as discussed previously, the delivery and return guide means can be incorporated into a double fiber optical delivery system used in association with a diagnostic radiator or an endoscope); a filter 28 which allows the passage of a selected portion of the infrared fluorescent spectrum; a photodiode 30, which may be a InGaAs or Silicon based photodiode; a box-car integrator 48 (or transient recorder combined with a signal averager) to amplify and process the electrical signal produced by the photodiode 30; and, an indicator 34 which produces an audio or visual signal when a detectable infrared fluorescence diagnostic signal is collected by the return guide means 26. It is again to be understood that the laser 46 may be tunable to deliver an excitation beam having a frequency selectable for maximum tissue penetration as taught by the present invention. It is also to be understood that various audio/visual indicators may be used to alert the physician and various delivery and return guide means can be used to deliver the excitation beam and collect the infrared fluorescence emissions. It is also within the inventors' contemplation to use a silicon vidicon in association with the present invention to generate a visual display corresponding to the infrared fluorescence emission pattern.

Obviously, many modifications and variations of the present invention are possible in light of the above teachings. It is therefore to be understood that within the scope of the appended claims that the invention may be practiced otherwise than as specifically described.

What is claimed and desired to be secured by Letters Patent of the United Patent is:

1. An apparatus for the localization of cancerous tumors found in animal or human tissue, wherein said cancerous tumors have absorbed a tumor-specific marker, said apparatus comprising:
   an optical excitation means for selectively radiating a portion of said tissue with excitation light in the red wavelength band;
   an optical detection means for detecting infrared fluorescence emitted by said tumor-specific marker, wherein the detection of said infrared fluorescence emissions identifies the presence of cancerous tumors in said radiated tissue; and,
   an indicator means, connected to said optical detection means for alerting the physician when said infrared fluorescence emission is detected.

2. The apparatus of claim 1, wherein said optical excitation means further comprises:
   an excitation source for generating light; and,
   a delivery guide means for selectively radiating a portion of said tissue with light from said excitation source.

3. The apparatus of claim 2, wherein said optical detection means further comprises:
   a return guide means for collecting light emitted from said radiated tissue;
   a filter means for selectively allowing the passage of the infrared component of light collected by said return guide means;
   a photodetector means for detecting the intensity of said infrared component and for generating a corresponding electrical signal; and a signal processing means operably connected to said photodetector means for amplifying and processing said electrical signal generated by said photodetector means.

4. The apparatus of claim 3, wherein said indicator means connects to said signal processing means for producing an acoustical signal for alerting the physician when said infrared fluorescence emissions are detected.

5. The apparatus of claim 3 wherein said indicator means connects to said signal processing means for producing a visual signal for alerting the physician when said infrared fluorescence emission is detected.

6. The apparatus of claim 1 or 3, wherein frequency of said excitation light is selected to optimize optical transmittance through said tissue and absorption by said tumor-specific marker, thereby causing fluorescence of said tumor-specific marker located at a maximum depth beneath said tissue surface.

7. The apparatus of claim 3, wherein said filter means allows the passage of an infrared diagnostic frequency band, said frequency band selected to provide sufficient spectral separation enabling said optical detection means to distinguish said infrared fluorescence emission from said excitation light reflected from said tissue.

8. The apparatus of claim 7, wherein said diagnostic frequency band is further selected to optimize optical transmittance through said tissue and the integrated infrared fluorescence signal.

9. The apparatus of claim 8, wherein said diagnostic frequency band is 9,000–13,000 Å.

10. The apparatus of claim 1, wherein said excitation light is in the 6,200–6,400 Å band.

11. The apparatus of claim 10, wherein said infrared fluorescence emission is detected in the 9,000–13,000 Å band.

12. The apparatus of claim 1, wherein said optical detection means detects the infrared fluorescence at a particular diagnostic frequency band, said diagnostic frequency band selected to provide sufficient spectral separation from said excitation light, thereby enabling said optical detection means to distinguish said infrared fluorescence emissions from said excitation light reflected from said tissue.

13. The apparatus of claim 11, wherein said diagnostic frequency band is further selected to optimize optical transmittance through said tissue by said infrared fluorescence.

14. An apparatus for the localization of cancer tumors found in animal or human tissue, wherein said cancer tumors have absorbed a tumor-specific marker, said apparatus comprising:
   an excitation source for generating long wavelength red light;
   a delivery guide means for selectively radiating a portion of said tissue with light from said excitation source;
   a return guide means for collecting light emitted from said radiated tissue;
   a filter means for selectively allowing passage of an infrared diagnostic band of infrared light collected by said return guide means;
   a photodetector means for detecting the intensity of infrared light passing through said filter means and for generating a corresponding electrical signal;
   a signal processing means operably connected to said photodetector means for amplifying and processing said electrical signal generated by said photodetector means and for generating an output signal in response to detecting infrared fluorescence emitted by said tumor-specific marker; and, an indicator means operably connected to said output of said signal processing means for alerting the physician when said infrared fluorescence emission is detected.

15. The apparatus of claim 14, wherein said infrared diagnostic band is selected to provide sufficient spectral separation from said long wavelength red excitation light, thereby enabling said photo detector to be substantially responsive to said infrared flourescence emitted by said tumor-specific marker.

16. The apparatus of claim 14, wherein said infrared diagnostic band is 9,000 thru 13,000 Å.

17. The apparatus of claim 14, wherein said indicator means provides an audio output alerting the physician when said infrared fluorescence emission is detected.

18. The apparatus of claim 14, wherein said indicator means provides a visual output alerting the physician when said infrared fluorescence emission is detected.

19. The apparatus of claim 14, wherein said excitation source produces pulsed emissions of said red light, and wherein said signal processing means is a box car integrator.

20. The apparatus of claim 14, wherein said excitation source provides a continuous emission of said red light, and wherein said signal processing means further comprises:
 a beam splitter in association with said excitation beam for spacially separating a component of said beam;
 a reference photodiode for detecting the amplitude of said excitation source; and,
 a lock-in-amplifier, connected to said reference photodiode and said photodetector means for providing an output signal in response to the detection of an infrared emission signal collected by said return guide means.

21. The apparatus of claim 14, wherein said delivery guide means and said return guide means each connect to a separate fiberoptic delivery system used in association with a diagnostic radiator.

22. The apparatus of claim 21, wherein said diagnostic radiator is an endoscope.

23. A method for the localization of cancer tumors found in animal or human tissue, said method comprising the steps of:
 injecting a patient with a tumor-specific marker;
 photoradiating a portion of said tissue with excitation light in the red wavelength band;
 optically detecting the intensity of infrared fluorescence emitted by said tumor-specific marker, wherein the detection of infrared fluorescence emissions identifies the presence of cancerous tumor in said radiated tissue; and,
 alerting the physician when said infrared fluorescence emissions are detected.

24. The method of claim 23, wherein said excitation light is in the 6,200–6,400 Å band.

25. The method of claim 23, wherein said step of optically detecting further comprises the steps of:
 collecting light emitted or reflected by said photoradiated tissue;
 filtering said collected light so as to only allow passage of light in an infrared diagnostic frequency band, said diagnostic frequency band selected to provide sufficient spectral separation from said excitation light, to allow resolution and detection of said infrared fluorescence emissions.

26. The method of claim 25 wherein said diagnostic frequency band is 9,000–13,000 Å.

27. The method of claim 23, wherein said tumor-specific marker is chosen from a group consisting of water soluble porphyrins.

28. The method of claim 23, wherein said tumor-specific marker is hematoporphyrin (HP).

29. The method of claim 23, wherein said tumor-specific marker is hematoporphyrin derivative (HPD).

30. The method of claim 23, wherein said tumor-specific marker is chosen from the group consisting of:
 hematoporphyrin (HP)
 hematoporphyrin derivative (HPD)
 tetra carboxyphenylporphine (TCPP)
 tetraphenylporphinesulfonate (TPPS)
 protoporphyrin
 coproporphyrin
 uroporphyrin.

31. The method of claim 23, wherein said tumor-specific marker is chosen from the group consisting of: riboflavin, fluorescein, acridine orange, tetracyclines and berberine sulfate.

* * * * *

UNITED STATES PATENT AND TRADEMARK OFFICE
CERTIFICATE OF CORRECTION

PATENT NO. : 4,541,438
DATED : September 17, 1985
INVENTOR(S) : Parker et al

It is certified that error appears in the above—identified patent and that said Letters Patent is hereby corrected as shown below:

In the designation of Inventors on the title page,

"William D. Standbro" should read --William D. Stanbro--

Signed and Sealed this

Seventeenth Day of December 1985

[SEAL]

Attest:

DONALD J. QUIGG

Attesting Officer

Commissioner of Patents and Trademarks